(12) United States Patent
Ooga et al.

(10) Patent No.: US 6,545,120 B1
(45) Date of Patent: Apr. 8, 2003

(54) PRODUCTION OF ALICYCLIC (METH)ALLYL ESTERS FOR PLASTIC LENS COMPOSITIONS

(75) Inventors: Kazuhiko Ooga, Oita (JP); Tsuneo Tajima, Oita (JP); Hiroshi Uchida, Oita (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 09/890,118

(22) PCT Filed: Jun. 14, 2001

(86) PCT No.: PCT/JP01/05081

§ 371 (c)(1),
(2), (4) Date: Jul. 26, 2001

(87) PCT Pub. No.: WO01/96274

PCT Pub. Date: Dec. 20, 2001

Related U.S. Application Data

(60) Provisional application No. 60/221,209, filed on Jul. 27, 2000.

(30) Foreign Application Priority Data

Jun. 16, 2000 (JP) .......................................... 2000-181489

(51) Int. Cl.[7] .............................................. C08G 63/78

(52) U.S. Cl. ..................... 528/275; 528/279; 528/296; 528/307; 525/437; 525/439; 526/282; 526/314; 526/318.4; 351/159; 351/179; 359/642

(58) Field of Search ................................ 528/275, 279, 528/296, 307; 525/437, 439; 526/282, 314, 318.4; 351/159, 179; 359/642

(56) References Cited

FOREIGN PATENT DOCUMENTS

| EP | 0 593 877 A1 | 4/1994 |
|----|---|---|
| WO | WO 96/27599 A1 | 9/1996 |
| WO | WO 99/17137 A1 | 4/1999 |
| WO | WO 99/38899 A1 | 8/1999 |

OTHER PUBLICATIONS

"Bis(2,2–Dimethyl–3–Hydroxypropyl) Esters of 1,4–, 1,3– and 1,2–Cyclohexanedicarboxylic Acids," Research Disclosure, 1993, pp. 818–821.

*Primary Examiner*—Samuel A. Acquah
(74) *Attorney, Agent, or Firm*—Sughrue Mion, PLLC

(57) ABSTRACT

An alicyclic (meth)allyl ester monomer obtained by a specific production process. An alicyclic (meth)allyl ester compound for plastic lenses, which can be obtained by a simple and easy production process and which can endure a long-term storages, is produced using the monomer, and a plastic lens is obtained using the compound.

3 Claims, 2 Drawing Sheets

PRODUCTION OF ALICYCLIC (METH)ALLYL ESTERS FOR PLASTIC LENS COMPOSITIONS

CROSS-REFERENCE TO RELATED APPLICATION

This application is an application filed under 35 U.S.C. §111(a) claiming benefit pursuant to 35 U.S.C. §119(e)(1) of the filing date of the Provisional Application No. 60/221,209 filed Jul. 27, 2000, pursuant to 35 §111(b).

TECHNICAL FIELD

The present invention relates to a process for producing a (meth)allyl ester monomer having an alicyclic structure within the molecule (hereinafter simply referred to as an "alicyclic (meth)allyl ester monomer") by transesterification of an alkyl ester of a polybasic acid having an alicyclic structure with a (meth)allyl ester, a process for producing an alicyclic (meth)allyl ester compound using an alicyclic (meth)allyl ester monomer produced by the above-described process and a polyhydric alcohol as starting materials, and an alicyclic (meth)allyl ester compound produced by this process.

The present invention also relates to a plastic lens composition containing the above-described alicyclic (meth) allyl ester compound, a plastic lens obtained by curing the composition, and a process for producing the plastic lens.

Still further, the present invention relates to a plastic lens composition comprising an alicyclic (meth)allyl ester compound, which can be used to produce a plastic lens while inhibiting generation of uneven dyeing and at the same time, preventing a mold from being damaged; a plastic lens obtained by curing the composition; and a process for producing the plastic lens.

The term "(meth)allyl alcohol" as used herein refers to an allyl alcohol, a methallyl alcohol and/or a mixture thereof. The term "(meth)allyl ester monomer" as used herein refers to an allyl ester monomer, a methallyl ester monomer and/or a mixture thereof. The term "(meth)allyl ester compound" as used herein refers to an allyl ester compound, a methallyl ester compound and/or a mixture thereof.

BACKGROUND ART

The alicyclic (meth)allyl ester monomer produced by reacting an alkyl ester of a polybasic acid having an alicyclic structure with an allyl alcohol or a methallyl alcohol is a highly reactive monomer. This monomer is used with various crosslinking agents or reactive diluting agents and the polymer of the monomer itself is widely used for various molded articles, laminates, decorative sheets and the like because of its excellent electrical properties, dimensional stability, heat resistance, weather resistance, chemical resistance and mechanical properties. In recent years, the polymer has also been found to have excellent optical properties and the use thereof as an optical material has begun.

The polyethylene glycol bis(allyl carbonate) resin which has been heretofore used is low in its polymerization reaction rate as compared with the acrylic resin, therefore, the polymerization reaction thereof is easy to control. As a result, a uniform polymerization reaction can be attained and the plastic lens derived from the polyethylene glycol bis (allyl carbonate) resin is advantageously small in the optical strain.

With respect to the dyeability of a plastic lens derived from the polyethylene glycol bis(allyl carbonate) resin, in the case where a plastic lens obtained by cast molding is dyed by the general means of dipping the lens in a dye bath at a high temperature, the dyeing density is known to be excellent as compared with plastic lenses derived from other resins.

However, the polydiethylene glycol bis(allyl carbonate) resin has a problem in that when a plastic lens derived from the resin is dyed, uneven dyeing is generated.

In order to overcome this problem, International Patent Publication Nos. WO99/17137 and WO99/38899 discloses use of an allyl ester compound containing a polycarboxylate structure having an alicyclic structure. In these publications, it is stated that uniform dyeing, which is required for the dyeability of plastic lens, can be attained, namely, an improved effect is provided on the reduction of uneven dyeing.

However, depending on the production process of an allyl ester monomer as a starting material, the above-described allyl ester compound sometimes fails in satisfying the requirement for long-term storage stability of the composition for optical materials represented by a lens.

Known examples of the production process for this kind of allyl ester monomer or methallyl ester monomer include:

1) a synthesis method starting from carboxylic acid chloride and an alcohol;
2) a synthesis method starting from an alkali salt of carboxylic acid and an alkyl halide; and
3) a synthesis method starting from carboxylic acid and an alcohol.

However, use of these methods in the production of compounds related to the present invention has a problem in that in the method 1), the acid chloride as a starting material is expensive.

In the case of applying the method 2), a side reaction of hydrolyzing the alkyl halide into a (meth)allyl alcohol takes place in a fairly high ratio and the operation of separating or recovering the starting materials and the by-product is disadvantageously complicated and costly.

In the method 3), a strong acid catalyst is generally used but the (meth)allyl alcohol is not stable to an acid catalyst usually used and has a problem in that di(meth)allyl ether is produced as a by-product. In addition to the low yield of (meth)allyl alcohol, it has been found that when sulfuric acid or p-toluenesulfonic acid is used as a catalyst, a corresponding allyl ester is produced as the by-product of the catalyst and these allyl sulfonate esters are difficult to separate from the objective alicyclic (meth)allyl ester monomer and in turn, the product is relatively low in the stability during a long-term storage and cannot cope with the use where the product is required to have a long-term storage stability, such as a composition for optical material use.

In this specification, the term "di(meth)allyl ether" refers to a diallyl ether, a dimethallyl ether and/or a mixture thereof.

DISCLOSURE OF INVENTION

By taking account of these problems in conventional techniques, it is an object of the present invention to provide a process for producing an alicyclic (meth)allyl ester monomer, comprising reacting an alkyl ester of a polybasic acid having an alicyclic structure, which has heretofore not been used as a starting material of the alicyclic (meth)allyl ester monomer, with a (meth)allyl alcohol in the presence of a transesterification catalyst, a process for producing an alicyclic (meth)allyl ester compound having a (meth)allyl ester group at the terminal, using the alicyclic (meth)allyl ester monomer, and the alicyclic (meth)allyl ester compound.

It is another object of the present invention to provide a plastic lens composition comprising the alicyclic (meth)allyl ester compound, which is suitable for the production of optical materials, particularly, a plastic lens, a plastic lens obtained by curing the plastic lens composition, and a process for producing the plastic lens.

As a result of extensive investigations to solve the above-described problems, the present inventors have found that, when a lower aliphatic alkyl ester of a polybasic acid having an alicyclic structure and a (meth)allyl alcohol are reacted by transesterification while distilling out a lower aliphatic alcohol, the objective alicyclic (meth)allyl ester monomer can be produced. Furthermore, it has been found that an alicyclic (meth)allyl ester compound having a (meth)allyl ester group at the molecular terminal can be produced using the alicyclic (meth)allyl ester monomer by a transesterification reaction with a polyhydric alcohol and also that this alicyclic (meth)allyl ester compound can be suitably used for optical use. The present invention has been accomplished based on these findings.

More specifically, the present invention (I) is a process for producing an alicyclic (meth)allyl ester monomer, comprising reacting an alkyl ester of a polybasic acid having an alicyclic structure with an allyl alcohol and/or a methallyl alcohol in the presence of a transesterification catalyst.

The present invention (II) is a process for producing an alicyclic (meth)allyl ester compound having a terminal structure of formula (1) and a repeating unit of formula (2), comprising transesterifying an alicyclic (meth)allyl ester monomer produced by the present invention (I) with a polyhydric alcohol in the presence of a catalyst. The present invention (II) includes an alicyclic (meth)allyl ester compound having a terminal structure of formula (1) and a repeating unit of formula (2), which is produced by the production process.

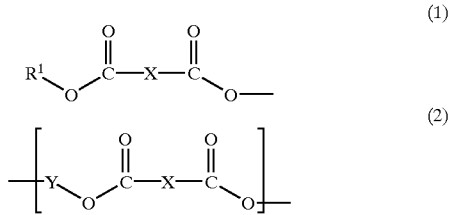

wherein each R¹ independently represents an allyl group or a methallyl group, each X independently represents an organic residue derived from a polyvalent carboxylic acid having an alicyclic structure, and each Y independently represents an organic residue derived from a polyhydric alcohol having from 2 to 20 carbon atoms and containing from 2 to 6 hydroxyl groups, provided that, by the ester bonding, X may have a branched structure having a terminal group of formula (1) and a repeating unit of formula (2) or may have R¹, and that by the ester bonding, Y may have a branched structure having a terminal group of formula (1) and a repeating unit of formula (2).

The present invention ,(III) is a plastic lens composition comprising an alicyclic (meth)allyl ester compound of the present invention (II).

The present invention (IV) is a plastic lens composition comprising at least one radical polymerization initiator in an amount of 0.1 to 10 parts by mass per 100 parts by mass of the entire curable component contained in the plastic lens composition.

The present invention (V) is a plastic resin obtained by curing the plastic lens composition of the present invention (III) or (IV).

The present invention (VI) is a process for producing the plastic lens of the present invention (V).

BRIEF DESCRIPTION OF DRAWINGS

The following figures are each a 400 MHz ¹H-NMR spectrum chart of an alicyclic allyl ester compound described in the examples.

BEST MODE FOR CARRYING OUT THE INVENTION

Figure 1:
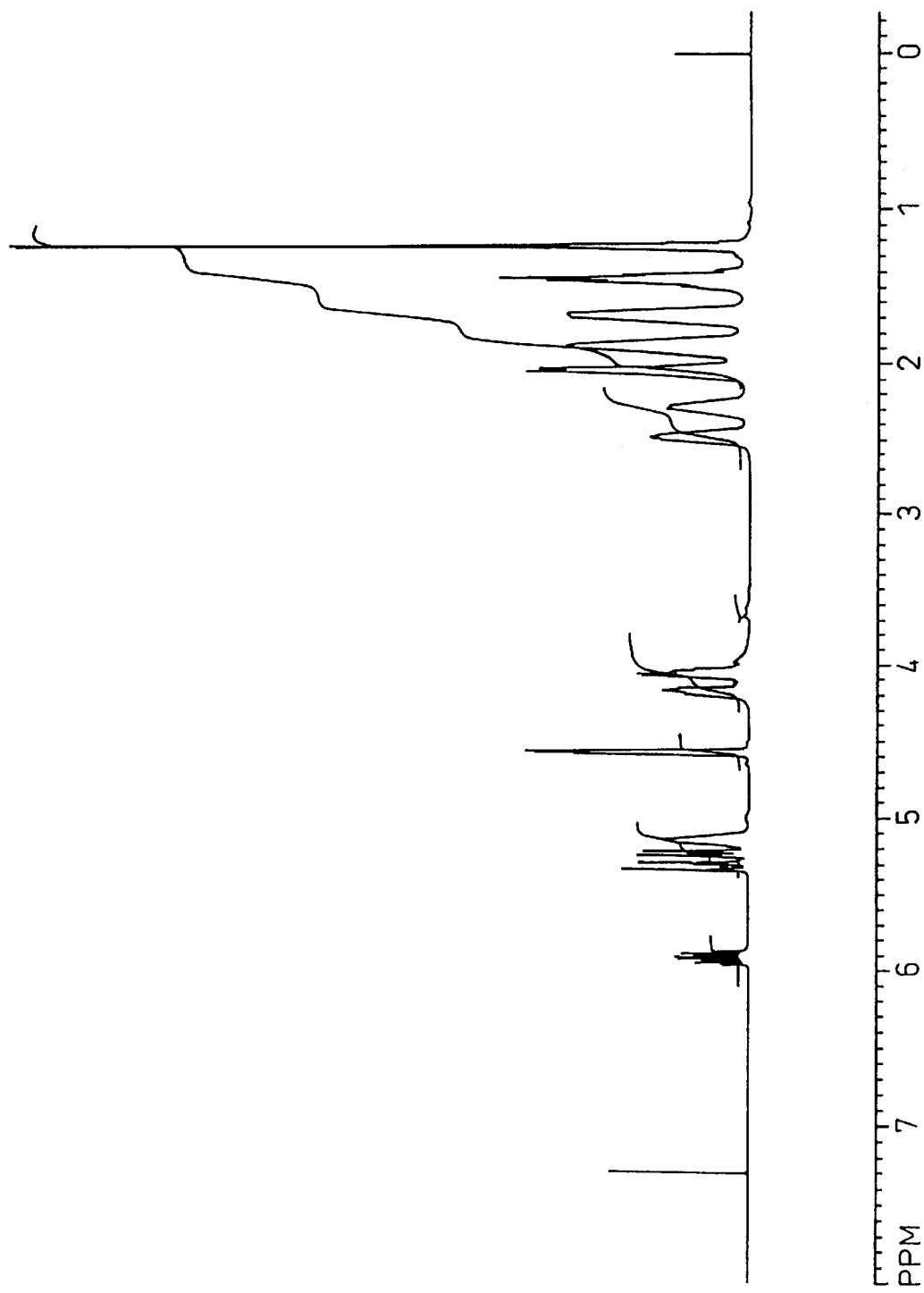
FIG. 1 is a 400 MHz ¹H-NMR spectrum chart of an alicyclic allyl ester compound obtained in Example 29.

The present invention is described in detail below.

The present invention (I) which is a process for producing an alicyclic (meth)allyl ester monomer is described below.

The ester of polybasic acid having an alicyclic structure for use in the present invention (I) is preferably a dicarboxylic acid ester, tricarboxylic acid ester or tetracarboxylic acid ester of a 5-, 6- or 7-membered cycloalkane which may have some other substituents. Examples thereof include diesters of 1,4-cyclohexanedicarboxylic acid, diesters of 1,3-cyclohexanedicarboxyic acid, triesters of 1,2,4-cyclohexanetricarboxylic acid, tetraesters of 1,2,4,5-cyclohexanetetracarboxylic acid, diesters of alkyl-substituted cyclohexane-1,4-dicarboxylic acid and diesters of halogen-substituted cyclohexane-1,4-dicarboxylic acid.

The term "alkyl" as used herein means an alkyl group having from 1 to 10 carbon atoms, which may have a branch, and specific examples thereof include a methyl group, an ethyl group, an n-propyl group, an iso-propyl group, an n-butyl group and a tert-butyl group. Specific examples of the "halogen" include chlorine, bromine and iodine.

Among those, on taking account of the reactivity, preferred are diesters of 1,4-cyclohexanedicarboxylic acid, diesters of 1,3-cyclohexanedicarboxylic acid, diesters of 5-alkyl-substituted cyclohexane-1,4-dicarboxylic acid and diesters of 5-halogen-substituted cyclohexane-1,4-dicarboxylic acid, more preferred are diesters of 1,4-cyclohexanedicarboxylic acid and diesters of 1,3-cyclohexanedicarboxylic acid.

The ester component in the polybasic acid ester having an alicyclic structure for use in the present invention (I) is not particularly limited as long as it has a group capable of transesterification. Specific examples thereof include a methyl group, an ethyl group, an isopropyl group, an n-propyl group, an isobutyl group, a sec-butyl group, a tert-butyl group and an n-butyl group. Among these, since the alcohol produced by the transesterification with a (meth)allyl alcohol is preferred to have a boiling point lower than that of the (meth)allyl alcohol, a methyl group, an ethyl group and an isopropyl group are preferred.

The term "alicyclic (meth)allyl ester monomer" as used herein refers to, as described above, a monomer which has an alicyclic structure within the molecule and at the same time, in which the carboxylic acid group directly bonded to the alicyclic structure has an ester structure based on the structure derived from the (meth)allyl alcohol.

Specific examples thereof include diallyl 1,4-cyclohexanedicarboxylate, dimethallyl 1,4-cyclohexanedicarboxylate, allylmethallyl 1,4-cyclohexanedicarboxylate, diallyl 1,3-cyclohexanedicarboxylate, dimethallyl 1,3- cyclohexanedicarboxylate, allylmethallyl 1,3-cyclohexanedicarboxylate, triallyl 1,2,4-cyclohexanetricarboxylate, trimethallyl 1,2,4-cyclohexkanetricarboxylate, allyldimethallyl 1,2,4-cyclohexanetricarboxylate, diallylmethallyl 1,2,4-cyclohexanetricarboxylate, tetrallyl 1,2,4,5-cyclohexanetetracarboylate, triallylmethallyl 1,2,4,5-cyclohexanetetracarboxylate, diallyldimethallyl 1,2,4,5-cyclohexanetetracarboxylate, allyltrimethallyl 1,2,4,5-cyclohexanetetracarboxylate, tetramethallyl 1,2,4,5-cyclohexanetetracarboxylate, diallyl 5-alkyl-substituted cyclohexane-1,4-dicarboxylate, allylmethallyl 5-alkyl-substituted cyclohexane-1,4-dicarboxylate, dimethallyl 5-alkyl-substituted cyclohexane-1,4-dicarboxylate, diallyl 5-halogen-substituted cyclohexane-1,4-dicarboxylate, allylmethallyl 5-halogen-substituted cyclohexane-1,4-dicarboxylate and dimethallyl 5-halogen substituted cyclohexane-1,4 -dicarboxylate.

The transesterification catalyst for use in the present invention (I) may, fundamentally, be any catalyst as long as it can activate the ester group and cause a reaction with an alcohol. Examples thereof include:

alkali metal elements, and oxides, weak acid salts, alcoholates and hydroxides thereof;

alkaline earth metal elements, and oxides, weak acid salts, alcoholates and hydroxides thereof;

Hf, Mn, U, Zn, Cd, Zr, Pb, Ti, Co and Sn elements, and oxides, hydroxides, inorganic acid salts, alkoxides, organic acid salts and organic metal complexes thereof;

organic metal compounds including organic tin compounds such as dibutyltin oxide, dioctyltin oxide and dibutyltin dichloride, and organic titanium compounds such as tetraalkyl titanates, e.g., tetramethyl titanate, tetraisopropyl titanate and tetrabutyl titanate; and tertiary amines such as dimethylaniline and 1,4-diazabicyclo[2.2.2]octane.

Among these, preferred are:

a combination of an alkali metal salt of organic acid and/or inorganic acid with a hydroxide and/or an oxide of alkaline earth metal;

organic tin compounds such as dibutyltin oxide, dioctyltin oxide and dibutyltin dichloride;

tetraalkyl titanates such as tetramethyl titanate, tetraisopropyl titanate and tetrabutyl titanate;

alkali metal salts and alkaline earth metal salts of carbonic acid, such as potassium carbonate and calcium carbonate;

alkyl alkoxides of an alkali metal, such as potassium methoxide, sodium methoxide, potassium ethoxide and potassium tert-butoxide;

tertiary amines such as dimethylaniline and 1,4-diazabicyclo[2.2.2]octane; and organic metal complexes of hafnium, such as hafnium acetylacetonate. These may be used in a combination of two or more thereof.

In particular, the combination of an alkali metal salt of organic acid and/or inorganic acid with a hydroxide and/or an oxide of alkaline earth metal is preferred, on taking account of production in industry, because the catalyst components precipitate after the completion of reaction and the product and the catalyst can be separated by only the filtration.

Specific examples of the hydroxide and the oxide of alkaline earth metal used as a catalyst include calcium hydroxide, magnesium hydroxide, barium hydroxide, calcium oxide and magnesium oxide. Among these, calcium hydroxide and calcium oxide are preferred in view of the capability.

Specific examples of the alkali metal salt of inorganic acid or organic acid present together include sodium acetate, potassium a cetate, lithium acetate, rubidium acetate, cesium acetate, potassium chloride, sodium chloride, sodium sulfate, potassium sulfate, potassium carbonate, sodium carbonate, lithium carbonate, rubidium carbonate, potassium phosphate, potassium nitrate, sodium hydrogencarbonate and cesium carbonate. Among these, potassium acetate, sodium acetate, rubidium acetate and cesium acetate are preferred in view of their capability.

Among the combinations of an alkali metal salt of organic acid and/or inorganic acid with a hydroxide and/or an oxide of alkaline earth metal, preferred are a combination of calcium hydroxide and cesium acetate, a combination of calcium oxide and cesium acetate, a combination of calcium hydroxide and rubidium acetate, a combination of calcium hydroxide and potassium acetate, a combination of calcium oxide and potassium acetate, a combination of calcium hydroxide and sodium acetate and a combination of calcium oxide and sodium acetate, and more preferred are a combination of calcium hydroxide and cesium acetate, a combination of calcium hydroxide and potassium acetate, a combination of calcium hydroxide and rubidium acetate and a combination of calcium oxide and potassium acetate.

With respect to the use ratio, the alkali metal salt of organic acid and/or inorganic acid is preferably used in an amount of 0.001 to 1 part by mass, more preferably from 0.01 to 0.5 part by mass, per 1 part by mass of the hydroxide and/or oxide of alkaline earth metal.

If the ratio of the alkali metal salt of organic acid and/or inorganic acid to the hydroxide and/or oxide of alkaline earth metal is less than this range, the reaction disadvantageously takes a long time, whereas if it exceeds this range, the reaction solution may be seriously colored and this is not preferred.

The reaction form used is a method of heating a polyvalent ester of polybasic acid having an alicyclic structure with a (meth)allyl alcohol in the presence of a catalyst. The reaction is preferably performed at a temperature of 30 to 200° C., more preferably from 50 to 150° C., under atmospheric pressure or applied pressure or if desired, under reduced pressure in an inert gas atmosphere. In order to more effectively perform the reaction, it is preferred to swiftly distill off the alcohols produced by the reaction scheme.

The (meth)allyl alcohol must be used at least in a theoretical amount to the starting material ester and on considering the reaction rate, equilibrium and the like, the (meth)allyl alcohol is preferably used in excess mol. However, if the (meth)allyl alcohol is used too excessively, an effect counterbalancing the excess amount is not brought out and this is not preferred in view of the profitability. Accordingly, the (meth)allyl alcohol is used in an amount of 1.2 to 10 times in mol, more preferably from 1.5 to 4 times in mol, based on the theoretical amount to the starting material ester. The starting material ester and the (meth)allyl alcohol may be charged at the beginning of the reaction or may be sequentially added on the way of the reaction.

The amount of the catalyst used is from 0.01 to 2% by mass, preferably on the order of 0.1 to 1% by mass. If the amount used is too small, the reaction rate decreases, whereas if the amount used exceeds the above-describe range, not only an effect counterbalancing the amount cannot be obtained but also serious coloration takes place or the yield rather decreases due to the side reaction. Moreover, the use in excess incurs a problem that the separation from the catalyst requires considerable time and labor.

The method for isolating the alicyclic (meth)allyl ester monomer produced in the reaction system of the present invention is prominently characterized in that when the above-described mixed catalyst is used, a purified product usable as a product can be obtained only by separating the catalyst using appropriate means such as filtration after the (meth)allyl alcohol is distilled off, and then subjecting the residue to acid washing and alkali washing.

Even in the case of using other catalysts, by purifying the reaction product using appropriate means such as distillation, a high-quality product can be obtained.

The present invention (II) is described below. The present invention (II) is a process for producing an alicyclic (meth) allyl ester compound having a terminal structure of formula (1) an d a repeating unit of formula (2), comprising transesterifying an alicyclic (meth)allyl ester monomer produced by the present invention (I) with a polyhydric alcohol in the presence of a catalyst. The present invention (II) includes an alicyclic (meth)allyl ester compound having a terminal structure of formula (1) and a repeating unit of formula (2), which is produced by this production process.

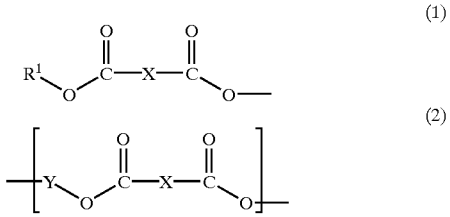

wherein each $R^1$ independently represents an allyl group or a methallyl group, each X independently represents an organic residue derived from a polyvalent carboxylic acid having an alicyclic structure, and each Y independently represents an organic residue derived from a polyhydric alcohol having from 2 to 20 carbon atoms and containing from 2 to 6 hydroxyl groups, provided that, by the ester bonding, X may have a branched structure having a terminal group of formula (1) and a repeating unit of formula (2) or may have $R^1$, and that by the ester bonding, Y may have a branched structure having a terminal group of formula (1) and a repeating unit of formula (2).

The alicyclic allyl ester compound having a terminal structure of formula (1) and a repeating unit of formula (2) for use in the present invention can be produced by transesterifying a (meth)allyl ester produced by the present invention (I) with a polyhydric alcohol in the presence of a catalyst.

The catalyst for use in the production step of the alicyclic allyl ester compound having a terminal structure of formula (1) and a repeating unit of formula (2) is not particularly limited as long as it is a catalyst which can be generally used in transesterification. An organic metal compound is preferred and specific examples thereof include tetraisopropoxy titanium, tetra-n-butoxy titanium, dibutyltin oxide, dioctyltin oxide, hafnium acetylacetonate and zirconium acetylacetonate, however, the present invention is not limited thereto. Among these, dibutyltin oxide and dioctyltin oxide are preferred.

The reaction temperature in this production step is not particularly limited, however, the reaction temperature is preferably from 100 to 230° C., more preferably from 120 to 200° C. In the case of using a solvent, the reaction temperature is sometimes limited by the boiling point of the solvent.

In this production step, a solvent is usually not used, however, a solvent may be used, if desired. The solvent which can be used is not particularly limited as long as it does not inhibit the transesterification. Specific examples thereof include benzene, toluene, xylene and cyclohexane, but the present invention is not limited thereto. Among these, benzene and toluene are preferred. However, as described above, this production step can also be performed without using a solvent.

The alicyclic allyl ester compound having a terminal structure of formula (1) and a repeating unit of formula (2), which is produced by the above-described production process, is described below.

In formula (1), each $R^1$ independently represents an allyl or methallyl group. In formula (1) or (2), each X independently represents an organic residue derived from a polyvalent carboxylic acid having an alicyclic structure.

The term "each $R^1$ independently represents an allyl group or a methallyl group" as used herein means that the terminal groups represented by formula (1) all may be an allyl group, all may be a methallyl group, partly may be allyl group or partly may be a methallyl group.

The term "each X independently represents" as used herein means that in the following structural formula (3) as one example of the repeating unit represented by formula (1) or (2), the Xs contained in the repeating structure are independent of each other.

This is described below by referring to, for example, structural formula (3) showing the case where Y is an organic residue derived from ethylene glycol:

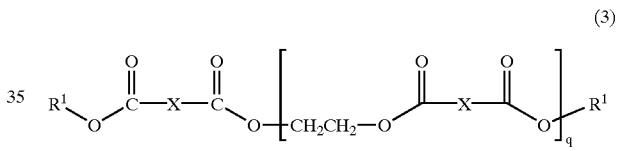

wherein each X independently represents an organic residue derived from a polyvalent carboxylic acid having an alicyclic structure and q represents 0 or an integer of 1 or more.

In structural formula (3), the Xs in the number of (q+1) may be organic residues all derived from polyvalent carboxylic acids having different alicyclic structures (namely, organic residues are derived one by one from polyvalent carboxylic acids having (q+1) kinds of alicyclic structures) or may be organic resides all derived from polyvalent carboxylic acids having the same alicyclic structure (namely, organic residues in the number of (q+1) derived from polyvalent carboxylic acids having one kind of alicyclic structure). A mixed structure may also be formed, where, out of the organic residues in the number of (q+1), some organic residues are derived from polyvalent carboxylic acids having the same alicyclic structure and some others are derived from polyvalent carboxylic acids having different kinds of alicyclic structures. Furthermore, the mixed structure may be completely random throughout the structure or, in the mixed structure, a part may be repeated.

When a part or all of Xs are an organic residue having three or more carboxyl groups and being derived from a polyvalent carboxylic acid having an alicyclic structure, a part or all of the Xs may have a branched structure having a terminal group of formula (1) and a repeating unit of formula (12) or may have $R^1$, through an ester bond. More specifically, when an organic residue derived from cyclohexane-1,2,4-tricarboxylic acid, as one example of the organic residue derived from a trivalent or greater valent carboxylic acid having an alicyclic structure, is present in the Xs, the alicyclic allyl ester compound as the present invention (II) having a terminal structure of formula (1) and a repeating unit of formula (2) may have a partial structure represented by the following structural formula (4):

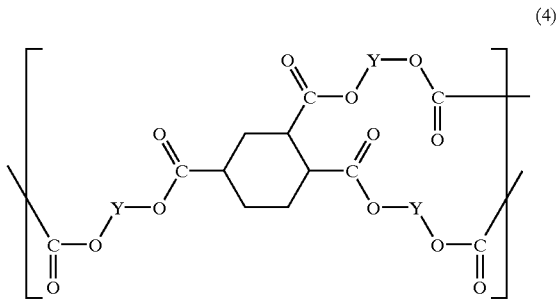

wherein each Y independently represents an organic residue derived from a polyhydric alcohol having from 2 to 20 carbon atoms and containing from 2 to 6 hydroxyl groups.

Of course, even when a part or all of the Xs are an organic residue derived from a polyvalent carboxylic acid having 3 or more carboxyl groups and having an alicyclic structure, each X may not have a branched structure at all.

The carboxylic groups may be retained as such. In particular, in the case where a part or all of the Xs is an organic residue derived from a polyvalent carboxylic acid having 3 or more carboxylic groups and having no branched structure, the carboxyl group in the moiety having no branched structure may be retained as such, but the alicyclic (meth)allyl ester compound of the present invention (II) may also include such a compound.

In formula (1) or (2), each X independently represents an organic residue derived from a polyvalent carboxylic acid having an alicyclic structure.

Specific examples of the "polyvalent carboxylic acid having an alicyclic structure", as used herein, include 1,2-cyclohexanedicarboxyliclacid, 1,3-cyclohexanedicarboxylic acid, 1,4-cyclohexanedicarboxylic acid, 4-methyl-cyclohexane-1,2-dicarboxylic acid, 3-methyl-cyclohexane-1,2-dicarboxylic acid and 1,2,4-cyclohexanetricarboxylic acid. Needless to say, the present invention is not limited thereto and these acids may be used individually or in combination of two or more thereof.

Among these polyvalent carboxylic acids having an alicyclic structure, in view of the flowability and transesterification property of the alicyclic allyl ester compound having a terminal structure of formula (1) and a repeating unit of formula (2), preferred are 1,2-cyclohexanedicarboxylic acid, 1,3-cyclohexanedicarboxylic acid, 1,4-cyclohexanedicarbxoylic acid, 4-methyl-cyclohexane-1,2-dicarboxylic acid, 3-methyl-cyclohexane-1,2-dicarboxylic acid and a mixture of two or more thereof, more preferred are 1,3-cyclohexanedicarboxylic acid, 1,4-cyclohexanedicarboxylic acid and a mixture thereof.

In formula (2), each Y independently represents an organic residue derived from a polyhydric alcohol having from 2 to 20 carbon atoms and containing from 2 to 6 hyroxyl groups.

The term "each Y independently represents" as used herein means that in the following formula (5) as one example of the repeating unit represented by formula (2), Ys in the number m, contained in the repeating structure, are independent of each other.

This is described below by referring to, for example, the following structural formula (5) showing the case where X is derived from 1,4-cyclohexanedicarboxylic acid.

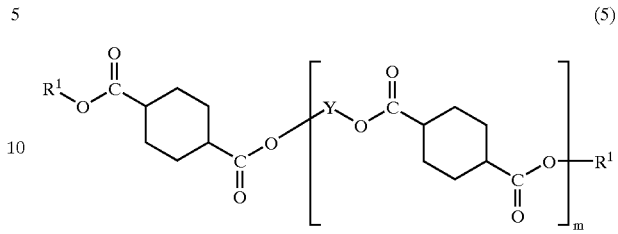

wherein each Y independently represents an organic residue derived from a polyhydric alcohol having from 2 to 20 carbon atoms and containing from 2 to 6 hydroxyl groups, and m represents 0 or an integer of 1 or more.

In the structural formula (5), the Ys in the number m may all be organic residues derived from different polyhydric alcohols (that is, organic residues are derived one by one from m kinds of polyhydric alcohols) or all may be organic residues derived from the same kind of polyhydric alcohol (that is, organic residues in the number m are derived from one kind of a polyhydric alcohol). A mixed structure may also be formed, where out of the Ys in the number m, some are organic residues derived from the same kind of polyhydric alcohol and some others are organic residues derived from different kinds of polyhydric alcohols. Furthermore, the mixed structure may be completely random throughout the structure or, in the mixed structure, a part may be repeated.

In the case where a part or all of the Ys are organic residues derived from a polyhydric alcohol having 3 or more hydroxyl groups, a part or all of the Ys can further have, by the ester bonding, a branched structure having a terminal group of formula (1) and a repeating unit of formula (2). More specifically, for example, when an organic residue derived from trimethylolpropane as one example of a trihydric alcohol is present in the Ys, the alicyclic allyl ester compound having a terminal structure of formula (I) and a repeating unit of formula (2) of the present invention (I) may have a partial structure represented by the following structural formula (6):

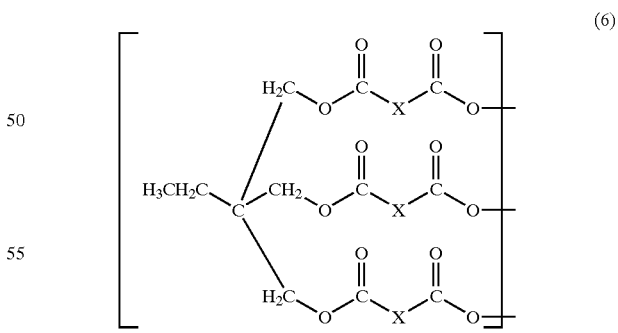

wherein each X independently represents an organic residue derived from a polyhydric carboxylic acid having an alicyclic structure.

Of course, even when apart or all of the Ys is an organic residue derived from a polyhydric alcohol having 3 or more hydroxyl groups, Y may not have a branched structure at all.

The hydroxyl groups may be retained as such. In particular, in the case where a part of all of the Ys is an organic residue derived from a polyhydric alcohol having 3 or more hydroxyl groups and having no branched structure, the hydroxyl group in the moiety having no branched structure may be retained as such, but the alicyclic (meth) allyl ester compound of the present invention (II) may also include such a compound.

In formula (2), each Y independently represents one or more kind of organic residue derived from a polyhydric alcohol having from 2 to 20 carbon atoms and containing from 2 to 6 hydroxyl groups. Examples of the "polyhydric alcohol having from 2 to 20 carbon atoms and containing from 2 to 6 hydroxyl groups" as used herein include the following compounds.

Specific examples of dihydric alcohols include ethylene glycol, propylene glycol, 1,3-propanediol, 1,4-butanediol, 1,3-butanediol, neopentyl glycol, hexamethylene glycol and 1,4-cyclohexanedimethanol.

Specific examples of trihydric or greater polyhydric alcohols include glycerin, trimethylolpropane, trimethylolethane, penthaerythritol, dipentaerythritol and sorbitol. In addition, dihydric alcohols containing an ether group in the main chain may be used, such as diethylene glycol, dipropylene glycol, triethylene glycol and polyethylene glycol. A mixture of two or more of these polyhydric alcohols may also be used. Needless to say, the present invention is not limited to these specific examples.

Among these polyhydric saturated alcohols, in view of the flowability of the allicyclic allyl ester compound having a terminal structure of formula (1) and a repeating unit of formula (12), preferred are propylene glycol, neopentyl glycol, 1,4-butanediol and diethylene glycol, and more preferred are propylene glycol and 1,4-butanediol.

The repeating number of the group represented by formula (2) is not particularly limited. A mixture of materials having various repeating numbers may also be used. Furthermore, a material having a repeating number of 0 may be used in combination with a material where the repeating number is an integer of 1 or more. However, use of only a compound where the repeating number is 0 is not preferred from the standpoint of achieving the object of the present invention.

Usually, the repeating number of the group represented by formula (2) as a repeating unit of the alicyclic allyl ester compound of the present invention (II) is preferably an integer of 1 to 50. If an alicyclic allyl ester compound comprising only a compound having a repeating number in excess of 50 is used for a plastic lens composition, the allyl group concentration decreases and this may cause adverse effects, for example, at the curing, the curing may be retarded or a part of the compound may remain uncured to reduce the physical properties such as mechanical properties of the cured product. In all compounds contained in the alicyclic allyl ester compound, the repeating number is preferably an integer from 1 to 50, more preferably from 1 to 30, still more preferably from 1 to 10.

Depending on the production conditions, the alicyclic (meth)allyl ester monomer as a starting material remains in the alicyclic allyl ester compound having a terminal structure of formula (1) and a repeating unit of formula (2), and this monomer may be used as it is in the plastic lens material. However, if the alicyclic (meth)allyl ester monomer as a starting material is present in 70% by mass or more based on the total amount of the alicyclic allyl ester compound of the present invention (II), when this compound is blended with the compound of formula (3) to prepare a plastic lens composition which is described later, dyeing specks may be disadvantageously generated or the mold may be damaged at the time of separating the cured product from the glass mold.

The plastic lens compositions of the present invention (III) and the present invention (IV) are described below. The present invention (III) is a plastic lens composition comprising an alicyclic (meth)allyl ester compound of the present invention (II).

The present invention (IV) is a plastic lens composition comprising at least one radical polymerization initiator in an amount of 0.1 to 10 parts by mass per 100 parts by mass of the entire curable component contained in the plastic lens composition.

The compound represented by formula (7) which may be contained in the plastic lens composition of the present invention (III) or the present invention (IV) can be synthesized by a conventional method. Examples thereof include a method of transesterifying a di(meth)allyl carbonate and a polyhydric alcohol in the presence of a catalyst (see, Japanese Examined Patent Publication No. 3-66327, JP-B-3-66327) and a method of reacting a (meth)allyl alcohol with phosgene and a polyhydric alcohol while performing dehydrochlorination (see, U.S. Pat. Nos. 2,370,565 and 2,592,058), but the present invention is not limited thereto.

The term "di(meth)allyl carbonate" as used herein means at least one compound selected from a diallyl carbonate, a dimethallyl carbonate, an allyl methallyl carbonate and a mixture thereof.

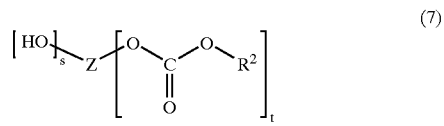

(7)

wherein Z represents one or more organic residues derived from a polyhydric saturated alcohol having from 2 to 20 carbon atoms and containing hydroxyl group in the number of n, n represents an integer of 2 to 6, $R^2$ represents an allyl group or a methallyl group, provided that each $R^2$ is independent, s represents an integer of 0 to (n−1), t is an integer of 1 to n, and s+t=n.

In formula (3), Z represents one or more organic residues derived from a polyhydric saturated alcohol having from 2 to 20 carbon atoms and containing from 2 to 6 hydroxyl groups. Examples of the "polyhydric saturated alcohol having from 2 to 20 carbon atoms and containing from 2 to 6 hydroxyl groups" as used herein include the following compounds.

Specific examples of dihydric saturated alcohols include ethylene glycol, propylene glycol, 1,3-propanediol, 1,4-butanediol, 1,3-butanediol, neopentyl glycol, hexamethylene glycol and 1,4-cyclohexane dimethanol.

Specific examples of trihydric or greater polyhydric saturated alcohols include glycerin, trimethylolpropane, trimethylolethane, penthaerythritol, dipentaerythritol and sorbitol. In addition, dihydric saturated alcohols containing an ether group in the main chain, such as diethylene glycol, dipropylene glycol, triethylene glycol or polyethylene glycol may also be used. A mixture of two or more of these alcohols may also be used. Needless to say, the present invention is not limited to these specific examples.

Among these polyhydric saturated alcohols, preferred are ethylene glycol, propylene glycol, diethylene glycol and dipropylene glycol, more preferred is diethylene glycol. When diethylene glycol is used as the polyhydric saturated alcohol, the poly(allyl carbonate) obtained is diethylene glycol bis(allyl carbonate) and specific examples thereof include CR-39, a trade name, produced by PPG, and Nouryset 20, a trade name, produced by Akzo Nobel.

In formula (7), $R^2$ represents an allyl group or a methallyl group, provided that each $R^2$ is independent. For example, when n is 3, the compound of formula (7) is a mixture of the compounds represented by the following structural formulae (8) to (10):

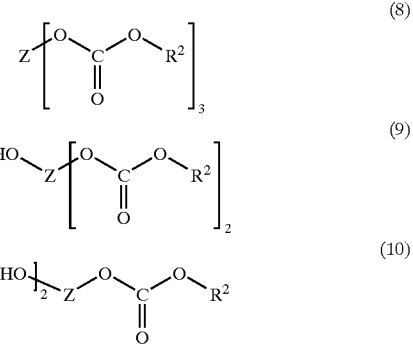

In these compounds, for example, in structural formula (8), the three $R^2$s may all be an allyl group or may all be a methallyl group. It is also possible that two $R^2$s are an allyl group and one $R^2$ is a methallyl group or that one $R^2$ is an allyl group and two $R^2$s are a methallyl group. Of course, the same applies to two $R^2$s in structural formula (9) and the $R^2$ in structural formula (10).

In formula (7), Z is one or more organic residues derived from a polyhydric saturated alcohol having from 2 to 20 carbon atoms and containing from 2 to 6 hydroxyl groups. If a plastic lens composition is produced using a compound having an organic residue as Z derived from a polyhydric saturated alcohol where the number of hydroxyl groups is an integer in excess of 6, the plastic lens obtained by curing the composition may be disadvantageously deteriorated in impact resistance. Also, if a plastic resin composition is produced using a compound having an organic residue as Z derived from a saturated alcohol where the number of hydroxyl groups is an integer of less than 2 (that is, 1), the plastic lens obtained by the curing is extremely reduced in heat resistance and solvent resistance and this is not preferred.

Assuming that the number of hydroxyl groups in Z is n, s is any one integer between 0 and n−1, t is any one integer between 1 and n, and s+t=n. In formula (7), t may be sufficient if it is an integer of at least 1 or more but in view of the physical properties of the final plastic lens, as many hydroxyl groups as possible are preferably substituted by carbonate groups. Although it may vary depending on the compositional ratio of respective compounds where t is less than n, the compound where t is n preferably accounts for 80% by mass or more, more preferably 90% by mass or more, in the compound represented by formula (7).

The amount of the alicyclic allyl ester compound of the present invention (II) blended is preferably from 0.1 to 20% by mass, more preferably from 1 to 15% by mass, still more preferably from 2 to 10% by mass, based on the entire curable component contained in the plastic lens composition of the present invention (III) or the present invention (IV). If the amount of the compound blended is less than 0.1% by mass, the effect of reducing uneven dyeing may not be brought out, whereas if the amount blended exceeds 20% by mass, the profitability disadvantageously decreases.

The term "entire curable component" as used herein means the total amount of the compound represented by formula (1), the compound represented by formula (2) and a monomer copolymerizable with the compound represented by formula (1) or the compound represented by formula (2).

The amount of the compound represented by formula (3) is 60 to 99.9% by mass, preferably from 75 to 99% by mass, more preferably from 80 to 98% by mass. If the amount blended is less than 60% by mass, the plastic lens obtained by curing the composition may be deteriorated in the mechanical properties and optical properties, whereas if it exceeds 99.9% by mass, dyeing failure disadvantageously occurs.

The plastic lens composition of the present invention (III) or the present invention (IV) may contain, mainly for the purpose of adjusting the viscosity of the composition, one or more monomers copolymerizable with the poly(allyl carbonate) represented by formula (7) or with the alicyclic allyl ester compound having a terminal structure of formula (1) and a repeating unit of formula (2), within the range not exceeding 20% by mass based, on the entire curable component contained in the plastic lens composition of the present invention.

Examples of the monomers include monomers having an acryl group, a vinyl group or an allyl group. Specific examples of the monomer having an acryl group include methyl (meth)acrylate and isobornyl (meth)acrylate; specific examples of the monomer having a vinyl group include vinyl acetate and vinyl benzoate; and specific examples of the monomer having an allyl group include diallyl 1,2-cyclohexane dicarboxylate, diallyl 1,3-cyclohexane dicarboxylate and diallyl 1,4-cyclohexane dicarboxylate. Of course, the present invention is not limited to these specific examples and within the range of not impairing the physical properties of the plastic lens obtained by curing, diallyl phthalate, diallyl terephthalate, diallyl isophthalate, allyl benzoate and the like may also be used.

On taking account of workability in the casting, the viscosity of the plastic lens composition of the present invention (III) or the present invention (IV) is generally in the range from 10 to 10,000 mPa·s at 25° C., preferably from 10 to 5,000 mPa·s, more preferably from 10 to 500 mPa·s.

The term "viscosity" as used herein means a viscosity measured by a rotational viscometer. The rotary viscometer is described in detail in *Iwanami Rikagaku Jiten* (*Iwanami Physics and Chemistry Encyclopedia*), 3rd ed., 8th imp. (Jun. 1, 1977).

The amount of the monomer added is 20% by mass or less, preferably 10% by mass or less, and more preferably 5% by mass or less, based on the entire curable component contained in the plastic lens composition of the present invention. If the monomer is added in excess of 20% by mass, the physical property values required for the plastic lens obtained by curing the composition, such as optical property, may be disadvantageously reduced. An optimal monomer is selected by taking account of the kind and the mixing ratio of poly(allyl carbonate) and allyl ester oligomer contained in the plastic lens composition and the physical property values, such as optical properties, required of the plastic lens obtained by curing.

The plastic lens composition of the present invention (IV) may contain a radical polymerization initiator as a curing agent and this is preferred.

The radical polymerization initiator which can be added to the plastic lens composition of the present invention (IV) is not particularly limited and a known radical polymerization initiator may be added as long as it does not adversely affect the physical property values, such as optical properties, of the plastic lens obtained by curing the composition.

The radical polymerization initiator for use in the present invention is, however, preferably soluble in other components present in the composition to be cured, and preferably generates free radicals at 30 to 120° C. Specific examples of the radical polymerization initiator which can be added include diisopropylperoxy dicarbonate, dicyclohexylperoxy dicarbonate, di-n-propylperoxy dicarbonate, di-sec-butylperoxy dicarbonate and tert-butyl perbenzoate, but the present invention is not limited thereto. In view of the curability, diisopropylperoxy dicarbonate is preferred.

The amount of the radical polymerization initiator added is in the range from 0.1 to 10 parts by mass, preferably from 1 to 5 parts by mass, based on the entire curable component contained in the plastic lens composition of the present invention. If the amount added is less than 0.1 part by mass, the composition may be insufficiently cured, whereas if it exceeds 10 parts by mass, the profitability disadvantageously decreases.

The plastic lens composition of the present invention (III) or the present invention (IV) may contain additives commonly used for the purpose of improving the performance of the plastic lens, such as a coloring agent including dye and pigment, an ultraviolet absorbent, a mold-releasing agent and an antioxidant.

Examples of the coloring agent include organic pigments such as an anthraquinone type, an azo type, a carbonium type, a quinoline type, a quinoneimine type, an indigoid type and a phthalocyanine type; organic dyes such as an azoic dye and a sulfur dye; and inorganic pigments such as titanium yellow, yellow iron oxide, zinc yellow, chrome orange, molybdenum red, cobalt violet, cobalt blue, cobalt green, chromic oxide, titanium oxide, zinc sulfide and carbon black.

Examples of the mold-releasing agent include stearic acid, butyl stearate, zinc stearate, stearic acid amide, fluorine-containing compounds and silicon compounds.

Examples of the ultraviolet absorbent include triazoles such as 2-(2'-hydroxy-tert-butylphenyl)benzo-triazole, benzophenones such as 2,4-dihydroxybenzophenone, salicylates such as 4-tert-butylphenyl salicylate, and hindered amines such as bis-(2,2,6,6-tetramethyl-4-piperidinyl) sebacate.

Examples of the antioxidant include phenols such as 2,6-di-tert-butyl-4-methylphenol and tetrakis[methylene-3-(3', 5'-di-tert-butyl-4-hydroxyphenyl)propionate]methane; sulfurs such as dilauryl-3,3'-thiodipropionlate; and phosphorus-containing antioxidants such as trisnonylphenylphosphite.

The total amount of the additives added, such as a coloring agent including dye and pigment, an ultraviolet absorbent, a mold-releasing agent and an antioxidant, is preferably 1% by mass or less based on the entire curable resin component contained in the plastic lens resin composition of the present invention.

The plastic lens of the present invention (V) is described below. The present invention (V) is a plastic lens obtained by curing the plastic lens composition of the present invention (III) or the present invention (IV).

The plastic lens of the present invention preferably has a refractive index of 1.497 to 1.505 at 25° C. The mold for use in the production of a plastic lens (refractive index: 1.498 at 25° C.) using the compound represented by formula (7) as a raw material is a mold suitable only for the production of plastics having the same refractive index. As long as the same mold is used, a change in the refractive index means a change in the capability of the lens.

For obtaining a plastic lens having the same ability from a composition for lenses having a high refractive index, a different mold is necessary. Accordingly, unless the refractive index of a lens obtained is limited so as to eliminate the necessity of changing the mold, the improvement in the properties of a lens attributable to the introduction of the alicyclic allyl ester compound having a terminal structure of formula (1) and a repeating unit of formula (2), the compound represented by formula (7), and the monomer copolymerizable with the alicyclic allyl ester compound having a terminal structure of formula (1) and a repeating unit of formula (2) or with the compound represented by formula (7), may not be achieved. The refractive index at 25° C. of the plastic lens of the present invention is preferably from 1.498 to 1.505, more preferably from 1.498 to 1.503.

The present invention (VI) is described below. The present invention (VI) is a production process of the plastic lens of the present invention (V), comprising curing the plastic lens composition of the present invention (III) or the present invention (IV).

In the present invention, the mold-working of the plastic lens composition is suitably performed by cast molding. Specific examples thereof include a method of adding a radical polymerization initiator to the composition, injecting the mixture through a line into a mold fixed by an elastomer, gasket or a spacer, and curing it under heating in an oven.

The constructive material of the mold used here is a metal or glass. In general, the mold for plastic lenses must be cleaned after the cast molding and such cleaning is usually performed using a strong alkali solution or a strong acid. Unlike a metal, glass is scarcely changed by the cleaning and furthermore, glass can be easily polished and thereby extremely reduced in the surface roughness. From these reasons, glass is preferably used.

The plastic lens composition of the present invention (III) or the present invention (IV) has an alicyclic structure, therefore, the refractive index can be easily approximated to the refractive index 1.498 of a plastic lens starting from polyethylene glycol bis(allyl carbonate) which is used for plastic lenses in many cases. This is advantageous in that the mold or the like conventionally used in the molding needs not be changed but can be used as it is.

The curing temperatures at molding is from about 30 to 120° C., preferably from 40 to 100° C. On taking account of shrinkage or strain at the curing, the curing temperature is preferably operated to allow the curing to gradually proceed while elevating the temperature. The curing time is generally from 0.5 to 100 hours, preferably from 3 to 50 hours, more preferably from 10 to 30 hours.

The method for dyeing the plastic lens of the present invention is not particularly limited. Any method may be used as long as it is a known dyeing method for plastic lenses. Among these, a dip dyeing method as a conventionally known ordinary method is preferred. The "dip dyeing method" as used herein means a method of dispersing a disperse dye together with a surfactant in water to prepare a dye bath and dipping a plastic lens in this dyeing solution under heating, thereby dyeing the plastic lens.

The method for dyeing the plastic lens is not limited to the dip dyeing method but other known methods may be used, such as a method of sublimating an organic pigment and thereby dyeing;a plastic lens (see, Japanese Examined Patent Publication No. 35-1384, JP-B-35-1384) and a method of sublimating a sublimable dye and thereby dyeing a plastic lens (see, Japanese Examined Patent Publication Nos. 56-159376 and 1-277814, JP-B-56-159376 and JP-B-1-277814). In view of simple operation, the dip dyeing method is most preferred.

The present invention is further illustrated below by referring to the following examples, however, the present invention should not be construed as being limited thereto.

The measurement conditions for gas chromatography (hereinafter simply referred to as "GC") and liquid chromatography (hereinafter simply referred to as "LC") employed in the examples are shown below.

GC Conditions

Apparatus used: GC-14B (manufactured by Shimadzu Corp.)

Detector: hydrogen flame ionization detector

Measuring method: internal standard method (internal standard substance: n-butyl acetate)

Injection temperature: 220° C.

Temperature condition: The temperature was kept at 40° C. for 10 minutes, thereafter elevated at a rate of 5° C./minute and then kept at 220° C. for 10 minutes.

Column used DB-WAX (produced by J & W), inner diameter: 0.25 mm, length: 30 m

LC Conditions

Eluent: aqueous 0.1 mass % phosphoric acid solution : acetonitrile=60:40 (v/v)

Flow rate: 1 ml/min

Detector: RI detector

Measuring method: internal standard method (internal standard substance: ethyl acetate)

Column used: 2 rolls in series of Shodex ODSpak F-511

Oven temperature: 40° C.

Various physical properties were measured as follows.

1. Refractive Index ($n_D$) and Abbe Number ($v_D$)

A test piece of 9 mm×16 mm×4 mm was prepared and measured on the refractive index ($n_D$) and Abbe number ($v_D$) at room temperature using "Abbe Refractometer 1T" manufactured by Atago. The contact solvent used was α-bromonaphthalene.

2. Viscosity

The viscosity was measured at 25° C. using Model B Viscometer (Model B8U) manufactured by Tokyo Keiki Co., Ltd.

3. Measuring Method of Hazen Color Number

The Hazen color number was measured by the method described in JIS K-0071-1.

4. Barcol Hardness

The Barcol hardness was measured using Model 934-1 according to JIS K-6911.

5. Dyeing Method and Evaluation of Uneven Dyeing

To a 1 l beaker, 0.8 g of Sumikaron Blue E-FBL (produced by Sumitomo Chemical Co., Ltd.) and 0.5 L of water were added and dissolved with stirring. The resulting solution was heated at 80° C. in a water bath and into this disperse dye solution, cured plastic lens samples each fixed to a holder so as not to overlap one on another were dipped at 8° C. for 10 minutes. Thereafter, the samples were taken out, thoroughly washed with water and then hot-air dried in an oven at 30° C.

The thus-obtained dyed plastic lens samples were observed with an eye and those failed in having a uniformly dyed appearance and revealed to have uneven dyeing were rated "defective". In the evaluation, 30 cured samples in total were used and the number of "defective" samples was counted.

EXAMPLE 1

Into a 300 ml three-neck flask with a thermometer and a rectifying tower, 100 g of dimethyl 1,4-cyclohexanedicarboxylate (hereinafter simply referred to as "CHDM"), 120 g of allyl alcohol, 0.25 g of calcium hydroxide and 0.05 g of potassium acetate were charged and reacted under heating in an oil bath adjusted to 120° C. The reaction was performed for 10 hours while distilling out methanol produced with the progress of the reaction from the rectifying tower. After the completion of reaction, it was confirmed by GC analysis that 98.8% of diallyl 1,4-cyclohexanedicarboxylate was produced based on CHDM. Thereafter, the allyl alcohol remaining in the system was distilled off under reduced pressure and the catalyst was removed by filtration. The filtrate was an almost colorless transparent liquid and the Hazen color number thereof was 5.

This filtrate was directly distilled under reduced pressure to obtain 121 g of colorless and transparent diallyl 1,4-cyclohexanedicarboxylate having a boiling point of 140 to 142° C./26.6 Pa (yield: 95%). The thus-obtained diallyl 1,4-cyclohexanedicarboxylate was designated as "Sample A".

EXAMPLE 2

A reaction was initiated under the same conditions as in Example 1 except for,changing 0.25 g of calcium hydroxide to 0.25 g of calcium oxide. The reaction time and the yield by GC are shown in Table 1.

EXAMPLE 3

A reaction was initiated under the same conditions as in Example 1 except for changing 0.25 g of calcium hydroxide to 0.25 g of magnesium hydroxide. The reaction time and the yield by GC are shown in Table 1.

EXAMPLE 4

A reaction was initiated under the same conditions as in Example 1 except for changing 0.25 g of barium hydroxide to 0.25 g of calcium oxide. The reaction time and the yield by GC are shown in Table 1.

TABLE 1

|  | Reaction Time | Yield by GC (based on CHDM) |
| --- | --- | --- |
| Example 1 | 10 hours | 98.8% |
| Example 2 | 20 hours | 93.2% |
| Example 3 | 34 hours | 67.9% |
| Example 4 | 20 hours | 91.4% |

EXAMPLE 5

A reaction was initiated under the same conditions as in Example 1 except for changing 0.05 g of potassium acetate to 0.05 g of sodium acetate. The reaction time and the yield by GC are shown in Table 2.

EXAMPLE 6

A reaction was initiated under the same conditions as in Example 1 except for changing 0.05 g of potassium acetate to 0.05 g of tripotassium phosphate. The reaction time and the yield by GC are shown in Table 2.

EXAMPLE 7

A reaction was initiated under the same conditions as in Example 1 except for changing 0.05 g of potassium acetate to 0.05 g of sodium hydrogen carbonate. The reaction time and the yield by GC are shown in Table 2.

EXAMPLE 8

A reaction was initiated under the same conditions as in Example 1 except for changing 0.05 g of potassium acetate to 0.05 g of potassium sulfate. The reaction time and the yield by GC are shown in Table 2.

EXAMPLE 9

A reaction was initiated under the same conditions as in Example 1 except for changing 0.05 g of potassium acetate to 0.05 g of potassium chloride. The reaction time and the yield by GC are shown in Table 2.

EXAMPLE 10

A reaction was initiated under the same conditions as in Example 1 except for changing 0.05 g of potassium acetate to 0.05 g of potassium carbonate. The reaction time and the yield by GC are shown in Table 2.

EXAMPLE 11

A reaction was initiated under the same conditions as in Example 1 except for changing 0.05 g of potassium acetate to 0.05 g of lithium carbonate. The reaction time and the yield by GC are shown in Table 2.

EXAMPLE 12

A reaction was initiated under the same conditions as in Example 1 except for changing 0.05 g of potassium acetate to 0.05 g of sodium carbonate. The reaction time and the yield by GC are shown in Table 2.

EXAMPLE 13

A reaction was initiated under the same conditions as in Example 1 except for changing 0.05 g of potassium acetate to 0.05 g of rubidium carbonate. The reaction time and the yield by GC are shown in Table 2.

TABLE 2

| Catalyst | Reaction Time | Yield by GC (based on CHDM) |
| --- | --- | --- |
| Example 5 | 14 hours | 93.6% |
| Example 6 | 11 hours | 94.6% |
| Example 7 | 13 hours | 91.9% |
| Example 8 | 16 hours | 95.1% |
| Example 9 | 17 hours | 94.7% |
| Example 10 | 16 hours | 97.2% |
| Example 11 | 38 hours | 91.3% |
| Example 12 | 25 hours | 94.9% |
| Example 13 | 15 hours | 96.8% |

EXAMPLE 14

Into a 300 ml three-neck flask with a thermometer and a rectifying tower, 100 g of CHDM, 149 g of methallyl alcohol, 0.25 g of calcium hydroxide and 0.05 g of potassium acetate were charged and reacted under heating in an oil bath adjusted to 120° C. The reaction was performed for 15 hours while distilling out methanol, produced with the progress of the reaction, from the rectifying tower. After the completion of reaction, it was confirmed by GC analysis that 94.0% of dimethallyl 1,4-cyclohexanedicarboxylate was produced based on CHDM.

EXAMPLE 15

A reaction was initiated under the same conditions as in Example 1 except for using 100 g of dimethyl 1,3-cyclohexanedicarboxylate in place of 100 g of CHDM. The reaction time and the yield by GC are shown in Table 3.

EXAMPLE 16

A reaction was initiated under the same conditions as in Example 1 except for using 100 g of dimethyl 1,2-cyclohexanedicarboxylate in place of 100 g of CHDM. The reaction time and the yield by GC are shown in Table 3.

EXAMPLE 17

A reaction was initiated under the same conditions as in Example 1 except for using 129 g of trimethyl 1,2,4-cyclohexanetricarboxylate in place of 100 g of CHDM. The reaction time and the yield by GC are shown in Table 3.

EXAMPLE 18

A reaction was initiated under the same conditions as in Example 1 except for using 158 g of tetramethyl 1,2,4,5-cyclohexanetetracarboxylate in place of 100 g of CHDM and changing the amount of allyl alcohol used from 120 g to 240 g. The reaction time and the yield by GC are shown in Table 3.

EXAMPLE 19

A reaction was initiated under the same conditions as in Example 1 except for using 114 g of diethyl 1,4-cyclohexanedicarboxylate in place of 100 g of CHDM. The reaction time and the yield, by GC are shown in Table 3.

EXAMPLE 20

A reaction was initiated under the same conditions as in Example 1 except for using 128 g of diisopropyl 1,4-cyclohexanedicarboxylate in place of 100 g of CHDM. The reaction time and the yield by GC are shown in Table 3.

TABLE 3

|  | Reaction Time | Yield by GC or LC (based on raw materials) |
| --- | --- | --- |
| Example 14 | 15 hours | 94.0% (GC) |
| Example 15 | 10 hours | 97.1% (GC) |
| Example 16 | 20 hours | 91.1% (GC) |
| Example 17 | 30 hours | 92.9% (LC) |
| Example 18 | 20 hours | 87.1% (LC) |
| Example 19 | 15 hours | 96.9% (GC) |
| Example 20 | 25 hours | 93.4% (GC) |

EXAMPLE 21

A reaction was initiated under the same conditions as in Example 1 except for using 2.0 g of calcium hydroxide in place of 0.25 g of calcium hydroxide and 0.05 g of potassium acetate. The reaction time and the yield by GC are shown in Table 4.

EXAMPLE 22

A reaction was initiated under the same conditions as in Example 1 except for using 1.0 g of potassium carbonate in place of 0.25 g of calcium hydroxide and 0.05 g of potassium acetate. The reaction time and the yield by GC are shown in Table 4.

EXAMPLE 23

A reaction was initiated under the same conditions as in Example 1 except for using 2.0 g of tetraisopropyl titanate in place of 0.25 g of calcium hydroxide and 0.05 g of potassium acetate. The reaction time and the yield by GC are shown in Table 4.

EXAMPLE 24

A reaction was initiated under the same conditions as in Example 1 except for using 2.0 g of sodium methoxide in place of 0.25 g of calcium hydroxide and 0.05 g of potassium acetate. The reaction time and the yield by GC are shown in Table 4.

EXAMPLE 25

A reaction was initiated under the same conditions as in Example 1 except that 2.0 g of calcium hydroxide was used in place of 0.25 g of calcium hydroxide and 0.05 g of potassium acetate, 2.0, g of dibutyltin oxide was used, the pressure was changed from atmospheric pressure to 0.6 MPa (gauge pressure) and the oil bath temperature was changed from 120° C. to 170° C. The reaction time and the yield by GC are shown in Table 4.

EXAMPLE 26

A reaction was initiated under the same conditions as in Example 1 except for using 2.0 g of zinc acetylacetonate in place of 0.25 g of calcium hydroxide and 0.05 g of potassium acetate. The reaction time and the yield by GC are shown in Table 4.

EXAMPLE 27

A reaction was initiated under the same conditions as in Example 1 except for using 2.0 g of hafnium acetylacetonate in place of 0.25 g of calcium hydroxide and 0.05 g of potassium acetate. The reaction time and the yield by GC are shown in Table 4.

EXAMPLE 28

A reaction was initiated under the same conditions as in Example 1 except for using 2.0 g of 1,4-diazabicyclo[2.2.2]octane in place of 0.25 g of calcium hydroxide and 0.05 g of potassium acetate. The reaction time and the yield by GC are shown in Table 4.

TABLE 4

|  | Reaction Time | Yield by GC (based on DMI) | Remarks |
| --- | --- | --- | --- |
| Example 21 | 18 hours | 95.8% | not colored |
| Example 22 | 12 hours | 96.2% | colored |
| Example 23 | 20 hours | 94.7% | slightly colored |
| Example 24 | 18 hours | 55.7% | colored |
| Example 25 | 25 hours | 95.9% | not colored |
| Example 26 | 30 hours | 40.7% | slightly colored |
| Example 27 | 25 hours | 90.5% | slightly colored |
| Example 28 | 15 hours | 95.0% | slightly colored |

COMPARATIVE EXAMPLE 1

Into the same reaction apparatus as in Example 1, 100 g of 1,4-cyclohexanecarboxylic acid, 120 g of allyl alcohol, 100 g of benzene and 1 g of sulfuric acid were charged and reacted under heating in an oil bath adjusted to 120° C. At the time when 23 g of water was precipitated, the reaction was terminated and the reaction product was analyzed by GC and found to contain 5% of diallyl ether (based on diallyl 1,4-cyclohexanecarboxylate). The solution was transferred to a 1 l separating funnel, 50 g of an aqueous 1% sodium hydroxide solution was charged there-into, a liquid separation operation was performed and the aqueous phase was removed. The same operation was again repeated, and then benzene and allyl alcohol in the oil phase was distilled off under reduced pressure by an evaporator. Thereafter, the components which were not distilled off by the evaporator were directly distilled under reduced pressure to obtain 177.7 g of diallyl 1,4-cyclohexanedicarboxylate as a slightly yellow transparent liquid (yield: 94%). The sulfur content of this liquid was analyzed by a chlorine-sulfur analyzer Model TSX-10 (manufactured by Mitsubishi Kagaku) and confirmed to be 30 ppm by mass. This diallyl 1,4-cyclohexnedicarboxylate was designated as "Sample B".

Evaluation of Storage Stability of Sample A and Sample B

Samples A and B immediately after the production and Samples A and B stored at 25° C. for 1 year after the production were measured on the Hazen color number. The results are shown in Table 5 below.

TABLE 5

|  | Hazen Color Number | |
| --- | --- | --- |
| Sample Used | Immediately after Production | Stored at 25° C. for 1 Year after Production |
| Sample A | less than 5 | less than 5 |
| Sample B | 5 | 15 |

EXAMPLE 29

Production of Alicyclic Allyl Ester Compound

Into a 1 l three-neck flask with a distilling unit, 120.0 g of Sample A, 24.1 g of propylene glycol and 0.12 g of dibutyltin oxide were charged. Under a nitrogen stream, the system was heated to 180° C. and the allyl alcohol generated was distilled off. When about 27.7 g of allyl alcohol was distilled off, the pressure inside the reaction system was reduced to 1.33 kPa to increase the distillation rate of allyl alcohol. After a theoretical amount of allyl alcohol was distilled off, the reaction system was heated for another one hour and then kept at 180° C. and 0.13 kPa for one hour. Thereafter, the reactor was cooled, then, 107.5 g of an allyl ester compound was obtained (hereinafter referred to as "Sample C").

The thus-obtained sample C was analyzed by gas chromatography (GC-14B, manufactured by Shimadzu Corp., using a hydrogen flame ionization detector and a column OV-17 of 0.5 m under a constant temperature condition of 160° C.) and found to contain 13% by mass of diallyl 1,4-cyclohexanedicarboxylate.

FIG. 1 shows the 400 MHz $^1$H-NMR spectrum of this sample.

COMPARATIVE EXAMPLE 2

Production of Alicyclic Allyl Ester Compound

Into a 1 l three-neck flask with a distilling unit, 120.0 g of Sample B, 24.1 g of propylene glycol and 0.12 g of dibutyltin oxide were charged. Under nitrogen stream, the system was heated at 180° C. and the allyl alcohol generated was distilled off. When about 27.7 g of allyl alcohol was distilled off, the pressure inside the reaction system was reduced to 1.33 kPa to increase the distillation rate of the allyl alcohol. After a theoretical amount of allyl alcohol was distilled off, the reaction system was heated for another one hour and kept at 180° C. and 0.13 kPa for one hour. Thereafter, the reactor was cooled, then, 107.5 g of an allyl ester compound was obtained (hereinafter referred to as "Sample D").

The thus-obtained sample D was analyzed by gas chromatography (GC-14B: manufactured by Shimadzu Corp., using a hydrogen flame ionization detector and a column OV-17 of 0.5 m under a constant temperature condition of 160° C.) and found to contain 12% by mass of diallyl 1,4-cyclohexanedicarboxylate.

Figure 2:
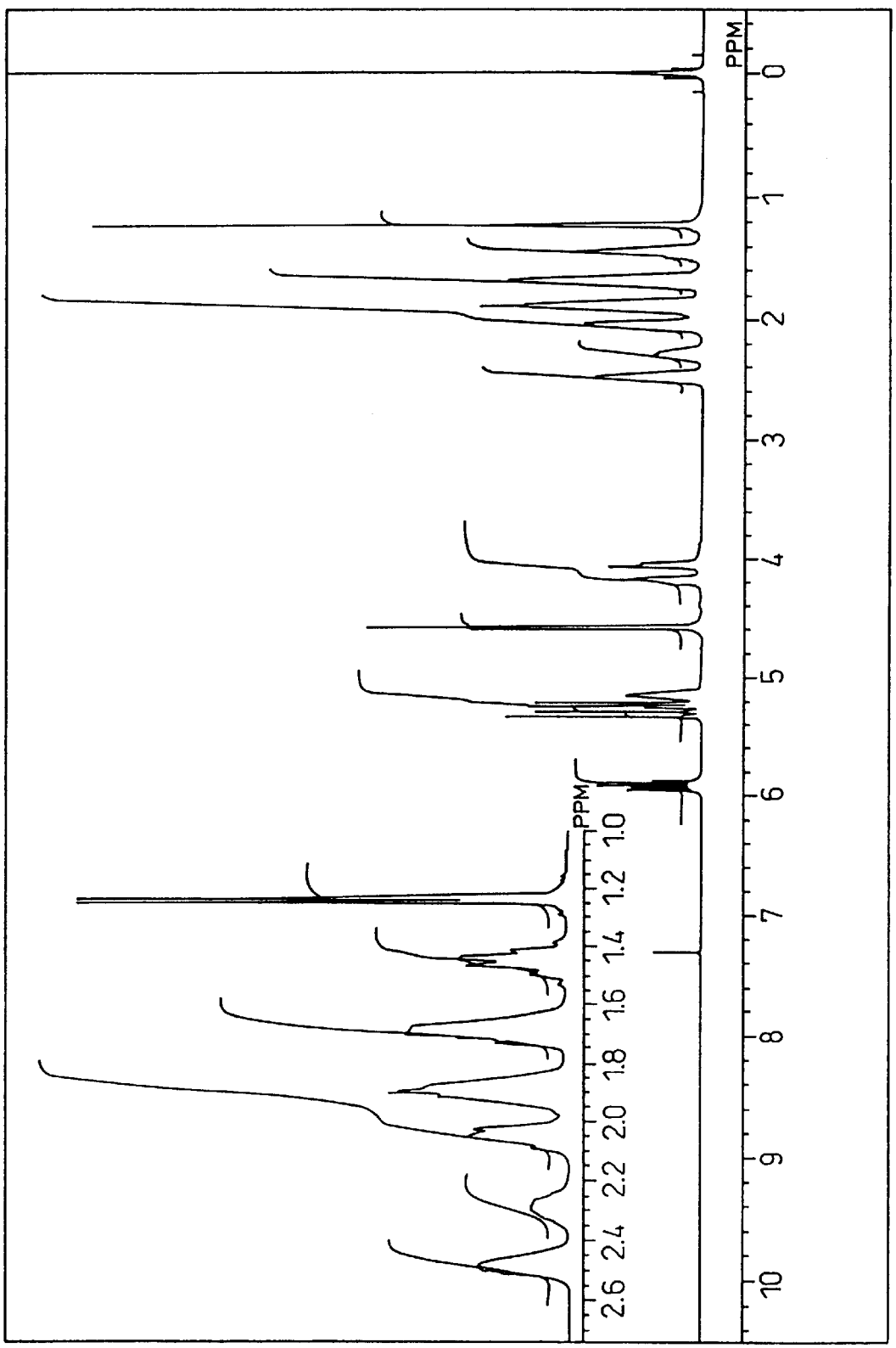
FIG. 2 is a 400 MHz ¹H-NMR spectrum chart of an alicyclic allyl ester compound obtained in Comparative Example 1.

FIG. 2 shows the 400 MHz $^1$H-NMR spectrum of this sample.

EXAMPLE 30

Measurement of Refractive Index, Abbe Number and Barcol Hardness of Lens, and Evaluation of Dyeing Speck As shown in Table 6, 95.0 parts by mass of diethylene glycol bis(allyl carbonate) (CR-39, a trade name, produced by PPG), 5 parts by mass of Sample C and 3 parts by mass of diisopropylperoxy dicarbonate (IPP) were blended and mixed with stirring to form a completely homogeneous solution composition. The viscosity at this time was measured. Thereafter, the vessel containing this solution was placed in a desiccator capable of depressurization and the pressure was reduced by a vacuum pump for about 15 minutes to deaerate gases in the solution. The resulting solution composition was injected by a syringe into a mold fabricated from a glass-made mold for ophthalmic plastic lenses and a resin-made gasket, while taking care to prevent intermixing of gas, and then cured in an oven according to a temperature program such that heating at 40° C. for 7 hours, heating at from 40° C. to 60° C. for 10 hours, heating at from 60° C. to 80° C. for 3 hours, heating at 80° C. for 1 hour and heating at 85° C. for 2 hours occurred.

The thus-obtained lens was measured for refractive index, Abbe number and Barcol hardness, and evaluated on uneven dyeing. The results thereof are shown in Table 6.

TABLE 6

|  |  | Example 30 | Comparative Example 3 | Comparative Example 4 |
|---|---|---|---|---|
| Blend (parts by mass) | Nouryset 200 | 95.0 | 95.0 | 100.0 |
|  | Sample C | 5.0 |  |  |
|  | Sample D |  | 5.0 |  |
| (25° C.) (mPa · s) |  | 28 | 28 | 25 |
| Initiator IPP (parts by mass) |  | 3 | 3 | 3 |
| Physical Properties | Refractive index ($n_D$) | 1.503 | 1.503 | 1.501 |
|  | Abbe number ($v_D$) | 55 | 55 | 58 |
|  | Barcol hardness | 31 | 31 | 33 |
|  | Uneven dyeing (number) | 1 | 1 | 10 |

COMPARATIVE EXAMPLES 3 and 4

Compositions were prepared to have a blend shown in Table 6 and in the same manner as in Example 1, the viscosity was measured and then the lens was measured for the refractive index, Abbe number and Barcol hardness and evaluated on uneven dyeing. The results are shown in Table 6.

INDUSTRIAL APPLICABILITY

According to the present invention, an alkyl ester of a polybasic acid having an alicyclic structure, which has been heretofore not used as a starting material of a (meth)allyl ester of a polybasic acid having an alicyclic structure, and a (meth)allyl alcohol are used and reacted in the presence of a transesterification catalyst to produce a corresponding alicyclic (meth)allyl ester monomer, whereby an industrial production process can be provided at a low cost with out producing any by-products such as diallyl ether and the product can have excellent long-term storage stability. The alicyclic (meth)allyl ester compound of the present invention produced from the alicyclic (meth)allyl ester monomer obtained by the above-described process and a polyhydric alcohol can provide a plastic lens having good dyeability by using it in combination with a poly(allyl carbonate) resin.

What is claimed is:

1. A process for producing an alicyclic (meth)allyl ester monomer, comprising reacting a polyvalent alkyl ester of a polybasic acid having an alicyclic structure with an allyl alcohol and/or a methallyl alcohol in the presence of a transesterification catalyst.

2. A process as claimed in claim 1, wherein the transesterification catalyst is at least one compound selected from the group consisting of combinations of alkali metal salts of organic acids and/or inorganic acids with hydroxides and/or oxides of alkaline earth metals, organic metal compounds, tertiary amines, alkali metal salts and/or alkaline earth metal salts of carbonic acid, and alkylalkoxides of alkali metals.

3. A process for producing an alicyclic (meth)allyl ester compound, comprising transesterifying an alicyclic (meth)allyl ester monomer produced by a process as set forth in claim 1 or 2 with a polyhydric alcohol in the presence of la catalyst, said alicyclic (meth)allyl ester compound having a terminal structure of the following formula (1) and a repeating unit of the following formula (2),

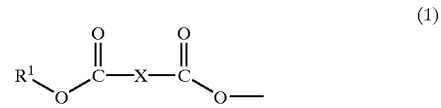

(1)

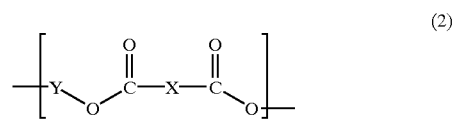

(2)

wherein each $R^1$ independently represents an allyl group or a methallyl group, each X independently represents an organic residue derived from a polyvalent carboxylic acid having an alicyclic structure, and each Y independently represents an organic residue derived from a polyhydric alcohol having from 2 to 20 carbon atoms and containing from 2 to 6 hydroxyl groups, provided that by the ester bonding, X may have a branched structure having a terminal group of formula (1) and a repeating unit of formula (2) or may have $R^1$, and that, by the ester bonding, Y may have a branched structure having a terminal group of formula (1) and a repeating unit of formula (2)).

* * * * *